(12) United States Patent
Eshel et al.

(10) Patent No.: US 7,347,855 B2
(45) Date of Patent: *Mar. 25, 2008

(54) NON-INVASIVE ULTRASONIC BODY CONTOURING

(75) Inventors: Yoram Eshel, Tel Aviv (IL); Ilia Vitsnudel, Even Yehuda (IL)

(73) Assignee: Ultrashape Ltd., Yokneam (IL)

( * ) Notice: Subject to any disclaimer, the term of this patent is extended or adjusted under 35 U.S.C. 154(b) by 988 days.

This patent is subject to a terminal disclaimer.

(21) Appl. No.: 10/021,238

(22) Filed: Oct. 29, 2001

(65) Prior Publication Data

US 2003/0083536 A1    May 1, 2003

(51) Int. Cl.
*A61N 5/06* (2006.01)
*A61B 17/22* (2006.01)

(52) U.S. Cl. .............................. 606/2.5; 606/2; 606/27; 606/32; 606/53; 601/2; 128/897; 128/898

(58) Field of Classification Search ................ 601/2–4; 600/437, 439, 443, 447; 606/128, 2.5, 27, 606/32, 53; 604/22, 19; 607/101; 128/897, 128/898

See application file for complete search history.

(56) References Cited

U.S. PATENT DOCUMENTS

| | | | |
|---|---|---|---|
| 3,637,437 A | 1/1972 | Goldberger | |
| 3,735,755 A * | 5/1973 | Eggleton et al. ................ | 601/3 |
| 4,043,946 A | 8/1977 | Sanker et al. | |
| 4,049,580 A | 9/1977 | Oden et al. | |
| 4,110,257 A | 8/1978 | O'Hare | |
| 4,116,804 A | 9/1978 | Needes | |
| 4,126,934 A | 11/1978 | Richter et al. | |
| 4,169,025 A | 9/1979 | Needes | |
| 4,450,056 A | 5/1984 | Gray | |
| 4,605,009 A | 8/1986 | Pourcelot et al. ........... | 128/660 |
| 4,826,799 A | 5/1989 | Cheng et al. | |
| 4,886,491 A | 12/1989 | Parisi et al. .................. | 604/22 |
| 4,938,216 A | 7/1990 | Lele ........................... | 128/399 |
| 4,986,275 A | 1/1991 | Ishida et al. ........... | 128/660.03 |
| 5,005,579 A | 4/1991 | Wurster et al. ........ | 120/660.03 |
| 5,079,952 A | 1/1992 | Nakaso et al. ................ | 73/624 |

(Continued)

FOREIGN PATENT DOCUMENTS

EP    1 060 728    12/2000

(Continued)

OTHER PUBLICATIONS

N.I. Vykhodtseva, et al., "Histologic Effects of high Intensity Pulsed Ultrasound Exposure with Subharmonic Emission in rabbit Brain In Vivo", Ultrasound in Med. & Biol., vol. 21, No. 7, pp. 969-979, 1995.

(Continued)

*Primary Examiner*—Brian L. Casler
*Assistant Examiner*—Joel Lamprecht
(74) *Attorney, Agent, or Firm*—EMPK & Shiloh, LLP

(57) ABSTRACT

A methodology and system for lysing adipose tissue including directing ultrasonic energy at a multiplicity of target volumes within the region, which target volumes contain adipose tissue, thereby to selectively lyse the adipose tissue in the target volumes and generally not lyse non-adipose tissue in the target volumes and computerized tracking of the multiplicity of target volumes notwithstanding movement of the body.

90 Claims, 8 Drawing Sheets

U.S. PATENT DOCUMENTS

| | | | | |
|---|---|---|---|---|
| 5,080,102 | A | 1/1992 | Dory | 128/660.03 |
| 5,111,822 | A | 5/1992 | Dory | 128/660.03 |
| 5,143,063 | A | 9/1992 | Fellner | 128/399 |
| 5,143,073 | A | 9/1992 | Dory | 128/660.03 |
| 5,209,221 | A | 5/1993 | Riedlinger | 128/24 AA |
| 5,211,164 | A * | 5/1993 | Allen | 600/426 |
| 5,219,401 | A | 6/1993 | Cathignol et al. | 128/660.03 |
| 5,301,660 | A | 4/1994 | Rattner | 601/4 |
| 5,419,761 | A * | 5/1995 | Narayanan et al. | 604/22 |
| 5,431,621 | A * | 7/1995 | Dory | 601/2 |
| 5,507,790 | A | 4/1996 | Weiss | 607/100 |
| 5,512,327 | A | 4/1996 | Chakraborty | |
| 5,526,815 | A | 6/1996 | Granz et al. | 128/660.03 |
| 5,618,275 | A | 4/1997 | Bock | 604/290 |
| 5,640,371 | A | 6/1997 | Schmidt et al. | 367/153 |
| 5,643,179 | A * | 7/1997 | Fujimoto | 601/2 |
| 5,827,204 | A | 10/1998 | Grandia et al. | 601/2 |
| 5,884,631 | A | 3/1999 | Silberg | 128/898 |
| 5,938,608 | A | 8/1999 | Bieger et al. | 600/439 |
| 5,944,663 | A * | 8/1999 | Kuth et al. | 600/411 |
| 5,948,011 | A | 9/1999 | Knowlton | 607/101 |
| 5,993,979 | A | 11/1999 | Figueroa et al. | |
| 6,038,467 | A * | 3/2000 | De Bliek et al. | 600/424 |
| 6,039,048 | A | 3/2000 | Silberg | 128/898 |
| 6,071,239 | A | 6/2000 | Cribbs et al. | 600/439 |
| 6,086,535 | A * | 7/2000 | Ishibashi et al. | 600/439 |
| 6,113,558 | A | 9/2000 | Rosenschein et al. | 601/2 |
| 6,206,873 | B1 | 3/2001 | Paolini et al. | 606/7 |
| 6,384,516 | B1 | 5/2002 | Fraser | 310/334 |
| 6,573,213 | B1 | 6/2003 | Ostgard et al. | |
| 6,645,162 | B2 * | 11/2003 | Friedman et al. | 601/2 |
| 6,684,097 | B1 * | 1/2004 | Parel et al. | 600/427 |
| 6,747,180 | B2 | 6/2004 | Ostgard et al. | |

FOREIGN PATENT DOCUMENTS

| | | |
|---|---|---|
| GB | 2 303 552 | 2/1997 |
| JP | 11-155894 | 6/1999 |
| WO | WO 95/03740 | 2/1995 |
| WO | WO 98/53787 | 12/1998 |
| WO | WO 00/53263 | 9/2000 |

OTHER PUBLICATIONS

Gail R. Ter Haar, et al., "Evidence for Acoustic Cavitation In Vivo: Thresholds for Bubble Formation with 0.75-MHz Continuous Wave and Pulsed Beams", IEEE Transactions on Ultrasonics, Ferroelectronics, and Frequency Control, vol. Uffc-33, No. 2, pp. 162-162, Mar. 1986.

T.G. Muir, et al., "Prediction of nonlinear acoustic effects at biomedical frequencies and intensities", Ultrasound in Med. & Biol., vol. 6, pp. 345-357, Pergamon Press Ltd., 1980.

Jahangir Tavakkoli, et al., "A Piezocomposite shock wave generator with electronic focusing capability: application for producing cavitation-induced lesions in rabbit liver", Ultrasound in Med. & Biol., vol. 23, No. 1, pp. 107-115, 1997.

Rod J. Rohrich, et al., "Comparative Lipoplasty Analysis of in Vivo-Treated Adipose Tissue", Plastic and Reconstruction Journal, 105:2152-2158, 2000.

* cited by examiner

NON-INVASIVE ULTRASONIC BODY CONTOURING

REFERENCE TO COMPUTER PROGRAM LISTING APPENDIX

A computer program listing appendix is submitted herewith on one compact disc and one duplicate compact disc. The total number of compact discs including duplicates is two. The files on the compact disc are software object code for carrying out a preferred embodiment of the invention. Their names, dates of creation, directory locations, and sizes in bytes are:

Directory apndx-A containing file TRACKOBJ.HEX (Appendix A) of Oct. 25, 2001 and of length 233,286 bytes.

The files are referred to herein as Appendix A. The material on the compact discs is incorporated by reference herein.

FIELD OF THE INVENTION

The present invention relates to lipolysis generally and more particularly to ultrasonic lipolysis.

BACKGROUND OF THE INVENTION

The following U.S. Pat. Nos. are believed to represent the current state of the art: U.S. Pat. Nos. 4,986,275; 5,143,063; 5,143,073; 5,209,221; 5,301,660; 5,431,621; 5,507,790; 5,526,815; 5,884,631; 6,039,048; 6,071,239; 6,113,558; 6,206,873

SUMMARY OF THE INVENTION

The present invention seeks to provide improved apparatus and methodology for ultrasonic lipolysis.

There is thus provided in accordance with a preferred embodiment of the present invention a method for lysing adipose tissue including the steps of:

directing focussed ultrasonic energy at a target volume in a region of a body containing adipose tissue; and modulating the focussed ultrasonic energy so as to selectively lyse the adipose tissue in the target volume and generally not lyse non-adipose tissue in the target volume.

Additionally in accordance with a preferred embodiment of the present invention, there is provided a method for lysing adipose tissue including the steps of:

generating, at a source outside a body, ultrasonic energy which selectively generally lyses adipose tissue and generally does not lyse non-adipose tissue; and directing the ultrasonic energy, from the source outside the body, at a target volume of a body containing adipose tissue.

Further in accordance with a preferred embodiment of the present invention there is provided a method for lysing adipose tissue including the steps of:

defining a region in a body at least partially by detecting spatial indications on the body; and directing ultrasonic energy at a multiplicity of target volumes within the region, which target volumes contain adipose tissue, thereby to selectively lyse the adipose tissue in the target volumes and generally not lyse non-adipose tissue in the target volumes.

Additionally in accordance with a preferred embodiment of the present invention, there is provided a method for lysing adipose tissue including the steps of:

directing ultrasonic energy at a multiplicity of target volumes within the region, which target volumes contain adipose tissue, thereby to selectively lyse the adipose tissue in the target volumes and generally not lyse non-adipose tissue in the target volumes; and computerized tracking of the multiplicity of target volumes notwithstanding movement of the body.

There is additionally provided in accordance with a preferred embodiment of the present invention apparatus for lysing adipose tissue including:

a focussed ultrasonic energy director, directing focussed ultrasonic energy at a target volume in a region of a body containing adipose tissue; and a modulator, cooperating with the energy director to produce a focussed ultrasonic energy so as to selectively lyse the adipose tissue in the target volume and generally not lyse non-adipose tissue in the target volume.

There is further provided in accordance with a preferred embodiment of the present invention apparatus for lysing adipose tissue including:

a source outside a body generating ultrasonic energy;

an ultrasonic energy director, which employs the ultrasonic energy to selectively generally lyse adipose tissue and generally not lyse non-adipose tissue in a target volume of a body containing adipose tissue.

There is additionally provided in accordance with a preferred embodiment of the present invention apparatus for lysing adipose tissue including the steps of:

a region definer, defining a region in a body at least partially by detecting spatial indications on the body; and a director, directing ultrasonic energy at a multiplicity of target volumes within the region, which target volumes contain adipose tissue thereby to selectively lyse the adipose tissue in the target volumes and generally not lyse non-adipose tissue in the target volumes.

There is still further provided in accordance with a preferred embodiment of the present invention apparatus for lysing adipose tissue including:

a director, directing ultrasonic energy at a multiplicity of target volumes within the region, which target volumes contain adipose tissue, thereby to selectively lyse the adipose tissue in the target volumes and generally not lyse non-adipose tissue in the target volumes; and computerized tracking functionality providing computerized tracking of the multiplicity of target volumes notwithstanding movement of the body.

Preferably, directing focussed ultrasonic energy generally prevents lysis of tissue outside of the target volume.

In accordance with a preferred embodiment of the present invention, the method also includes ultrasonic imaging of the region at least partially concurrently with directing the focussed ultrasonic energy at the target volume.

Preferably, directing includes positioning at least one ultrasonic transducer relative to the body in order to direct the focussed ultrasonic energy at the target volume.

The directing may also include varying the focus of at least one ultrasonic transducer in order to direct the focussed ultrasonic energy at the target volume. Varying the focus may change the volume of the target volume, and/or the distance of the target volume from the at least one ultrasonic transducer.

The directing may also include positioning at least one ultrasonic transducer relative to the body in order to direct the focussed ultrasonic energy at the target volume.

The method preferably also includes sensing ultrasonic energy coupling to an external surface of the body adjacent the target volume.

The method preferably additionally includes sensing of cavitation at the target volume.

Preferably, directing takes place from an ultrasonic transducer located outside of the body.

In accordance with a preferred embodiment of the present invention, the ultrasonic energy has a frequency in a range of 50 KHz-1000 KHz, more preferably in a range of 100 KHz-500 KHz, and most preferably in a range of 150 KHz-300 KHz.

Preferably, the modulating provides a duty cycle between 1:2 and 1:250, more preferably between 1:5 and 1:30 and most preferably between 1:10 and 1:20.

In accordance with a preferred embodiment of the present invention, the modulating provides between 2 and 1000 sequential cycles at an amplitude above a cavitation threshold, more preferably between 25 and 500 sequential cycles at an amplitude above a cavitation threshold and most preferably between 100 and 300 sequential cycles at an amplitude above a cavitation threshold.

Preferably, the modulating includes modulating the amplitude of the ultrasonic energy over time.

Preferably, directing includes directing focussed ultrasonic energy at a multiplicity of target volumes in a time sequence.

In accordance with a preferred embodiment of the present invention, directing includes directing focussed ultrasonic energy at plural ones of the multiplicity of target volumes at times which at least partially overlap.

Preferably, at least some of the multiplicity of target volumes at least partially overlap in space.

In accordance with a preferred embodiment of the present invention, the method includes defining the region by marking at least one surface of the body. The method may also include defining the region by selecting at least one depth in the body and/or by detecting adipose tissue in the body and/or by detecting non-lysed adipose tissue.

Preferably, directing also includes defining the target volumes as unit volumes of non-lysed adipose tissue within the region.

In accordance with a preferred embodiment of the present invention, modulating the ultrasonic energy so as to selectively lyse the adipose tissue in the multiplicity of target volumes proceeds sequentially in time wherein selective lysis of adipose tissue in each target volume takes place only following detection of non-lysed adipose tissue therein.

Preferably, the method also includes computerized tracking of the multiplicity of target volumes notwithstanding movement of the body.

Preferably, the computerized tracking includes sensing changes in the position of markings on the body and employing sensed changes for tracking the positions of the target volumes in the body.

Preferably, the modulation provides a decreasing amplitude over time which exceeds a cavitation threshold.

BRIEF DESCRIPTION OF THE DRAWINGS

The present invention will be understood and appreciated more fully from the following detailed description, taken in conjunction with the drawings in which.

BRIEF DESCRIPTION OF SOFTWARE APPENDIX

Appendix A is software listing of computer software is object code on a CD ROM for carrying out a preferred embodiment of the invention in accordance with the best mode known to the inventors.

DETAILED DESCRIPTION OF PREFERRED EMBODIMENTS

Figure 1:
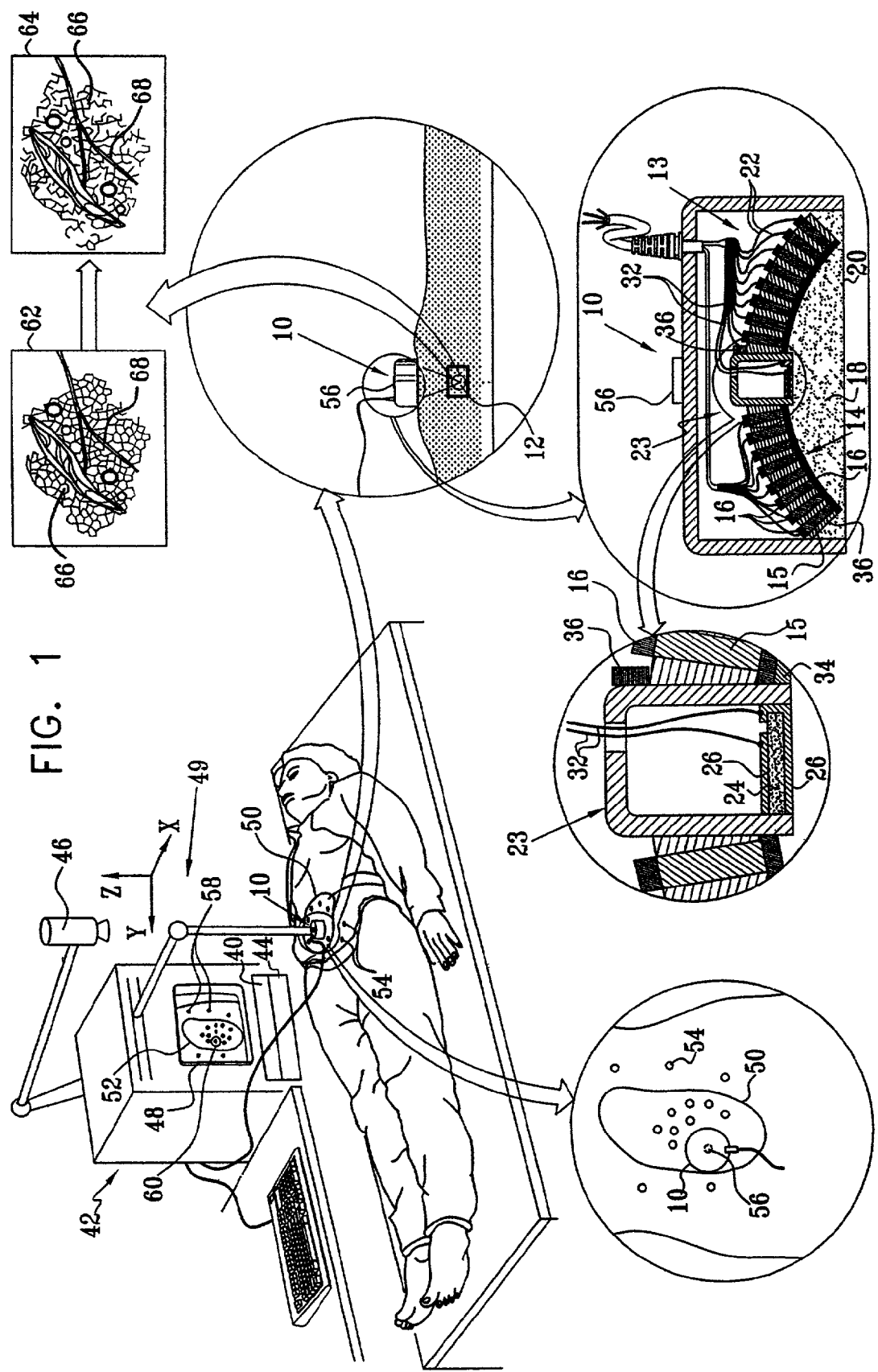
FIG. 1 is a simplified pictorial illustration of the general structure and operation of ultrasonic lipolysis apparatus constructed and operative in accordance with a preferred embodiment of the present invention.

Reference is now made to FIG. 1, which is a simplified pictorial illustration of the general structure and operation of ultrasonic lipolysis apparatus constructed and operative in accordance with a preferred embodiment of the present invention. As seen in FIG. 1, an ultrasonic energy generator and director, such as an ultrasonic transducer 10, disposed outside a body, generates ultrasonic energy which, by suitable placement of the transducer 10 relative to the body, is directed to a target volume 12 inside the body and is operative to selectively generally lyse adipose tissue and generally not lyse non-adipose tissue in the target volume.

A preferred embodiment of ultrasonic energy generator and director useful in the present invention comprises an ultrasonic therapeutic transducer 13 including a curved phased array 14 of piezoelectric elements 15, typically defining a portion of a sphere or of a cylinder, and having conductive coatings 16 on opposite surfaces thereof. The piezoelectric elements 15 may be of any suitable configuration, shape and distribution. An intermediate element 18, formed of a material, such as polyurethane, which has acoustic impedance similar to that of soft mammalian tissue, generally fills the curvature defined by phased array 14 and defines a contact surface 20 for engagement with the body, typically via a suitable coupling gel (not shown). Contact surface 20 may be planar, but need not be.

Suitably modulated AC electrical power is supplied by conductors 22 to conductive coatings 16 to cause the piezoelectric elements 15 to provide a desired focussed acoustic energy output.

In accordance with a preferred embodiment of the present invention an imaging ultrasonic transducer subassembly 23 is incorporated within transducer 10 and typically comprises a piezoelectric element 24 having conductive surfaces 26 associated with opposite surfaces thereof. Suitably modulated AC electrical power is supplied by conductors 32 to conductive surfaces 26 in order to cause the piezoelectric element 24 to provide an acoustic energy output. Conductors 32, coupled to surfaces 26, also provide an imaging output from imaging ultrasonic transducer subassembly 23.

It is appreciated that any suitable commercially available ultrasonic transducer may be employed or alternatively, imaging ultrasonic transducer subassembly 23 may be eliminated.

It is further appreciated that various types of ultrasonic transducers 10 may be employed. For example, such transducers may include multiple piezoelectric elements, multi-layered piezoelectric elements and piezoelectric elements of various shapes and sizes arranged in a phase array.

In a preferred embodiment of the present invention shown in FIG. 1, the ultrasonic energy generator and director are combined in transducer 10. Alternatively, the functions of generating ultrasonic energy and focussing such energy may be provided by distinct devices.

In accordance with a preferred embodiment of the present invention, a skin temperature sensor 34, such as an infrared sensor, may be mounted alongside imaging ultrasonic transducer subassembly 23. Further in accordance with a preferred embodiment of the present invention a transducer temperature sensor 36, such as a thermocouple, may also be mounted alongside imaging ultrasonic transducer subassembly 23.

Figure 2:
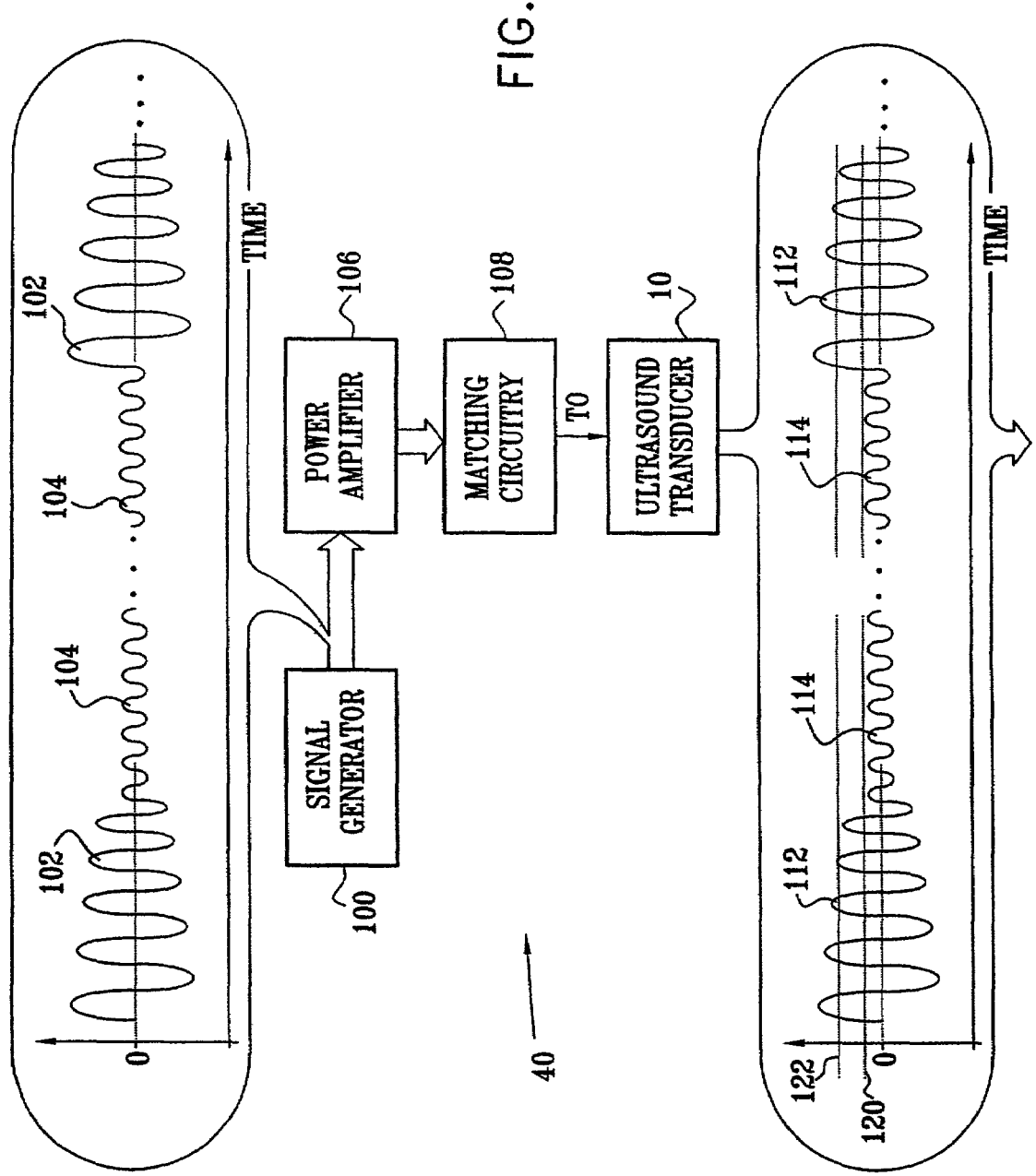
FIG. 2 is a simplified block diagram illustration of a preferred power source and modulator showing a pattern of variation of ultrasonic pressure over time in accordance with a preferred embodiment of the present invention.

Ultrasonic transducer 10 preferably receives suitably modulated electrical power from a power source and modulator assembly 40, forming part of a control subsystem 42. Control subsystem 42 also typically includes a lipolysis control computer 44, having associated therewith a camera 46, such as a video camera, and a display 48. A preferred embodiment of power source and modulator assembly 40 is illustrated in FIG. 2 and described hereinbelow. Ultrasonic transducer 10 is preferably positioned automatically or semi-automatically as by an X-Y-Z positioning assembly 49. Alternatively, ultrasonic transducer 10 may be positioned at desired positions by an operator.

In accordance with a preferred embodiment of the present invention, camera 46 is operative for imaging a portion of the body on which lipolysis is to be performed. A picture of the portion of the patient's body viewed by the camera is preferably displayed in real time on display 48.

An operator may designate the outline of a region containing adipose tissue. In accordance with one embodiment of the present invention, designation of this region is effected by an operator marking the skin of a patient with an outline 50, which outline is imaged by camera 46 and displayed by display 48 and is also employed by the lipolysis control computer 44 for controlling the application of ultrasonic energy to locations within the region. A computer calculated representation of the outline may also be displayed on display 48, as designated by reference numeral 52. Alternatively, the operator may make a virtual marking on the skin, such as by using a digitizer (not shown), which also may provide computer calculated outline representation 52 on display 48.

In addition to the outline representation 52, the functionality of the system of the present invention preferably also employs a plurality of markers 54 which are typically located outside the region containing adipose tissue, but may be located inside the region designated by outline 50. Markers 54 are visually sensible markers, which are clearly seen by camera 46, captured by camera 46 and displayed on display 48. Markers 54 may be natural anatomic markers, such as distinct portions of the body or alternatively artificial markers such as colored stickers. These markers are preferably employed to assist the system in dealing with deformation of the region nominally defined by outline 50 due to movement and reorientation of the body. Preferably, the transducer 10 also bears a visible marker 56 which is also captured by camera 46 and displayed on display 48.

Markers 54 and 56 are typically processed by computer 44 and may be displayed on display 48 as respective computed marker representations 58 and 60 on display 48.

FIG. 1 illustrates the transducer 10 being positioned on the body over a location within the region containing adipose tissue. Blocks designated by reference numerals 62 and 64 show typical portions of a region containing adipose tissue, respectively before and after lipolysis in accordance with a preferred embodiment of the invention. It is seen from a comparison of blocks 62 and 64 that, in accordance with a preferred embodiment of the present invention, within the region containing adipose tissue, the adipose tissue, designated by reference numeral 66, is lysed, while non-adipose tissue, such as connective tissue, designated by reference numeral 68, is not lysed.

Reference is now FIG. 2, which is a simplified block diagram illustration of a preferred power source and modulator assembly 40 (FIG. 1), showing a pattern of variation of ultrasonic pressure over time in accordance with a preferred embodiment of the present invention. As seen in FIG. 2, the power source and modulator assembly 40 preferably comprises a signal generator 100 which provides a time varying signal which is modulated so as to have a series of relatively high amplitude portions 102 separated in time by a series of typically relatively low amplitude portions 104. Each relatively high amplitude portion 102 preferably corresponds to a cavitation period and preferably has a decreasing amplitude over time.

Preferably the relationship between the time durations of portions 102 and portions 104 is such as to provide a duty cycle between 1:2 and 1:250, more preferably between 1:5 and 1:30 and most preferably between 1:10 and 1:20.

Preferably, the output of signal generator 100 has a frequency in a range of 50 KHz–1000 KHz, more preferably between 100 KHz–500 KHz and most preferably between 150 KHz–300 KHz.

The output of signal generator 100 is preferably provided to a suitable power amplifier 106, which outputs via impedance matching circuitry 108 to an input of ultrasonic transducer 10 (FIG. 1), which converts the electrical signal received thereby to a corresponding ultrasonic energy output. As seen in FIG. 2, the ultrasonic energy output comprises a time varying signal which is modulated correspondingly to the output of signal generator 100 so as to having a series of relatively high amplitude portions 112, corresponding to portions 102, separated in time by a series of typically relatively low amplitude portions 114, corresponding to portions 104.

Each relatively high amplitude portion 102 preferably corresponds to a cavitation period and has an amplitude at a target volume 12 (FIG. 1) in the body which exceeds a cavitation maintaining threshold 120 and preferably has a decreasing amplitude over time. At least an initial pulse of each relatively high amplitude portion 112 has an amplitude at the target volume 12, which also exceeds a cavitation initiation threshold 122.

Relatively low amplitude portions 114 have an amplitude which lies below both thresholds 120 and 122.

Preferably the relationship between the time durations of portions 112 and portions 114 is such as to provide a duty cycle between 1:2 and 1:250, more preferably between 1:5 and 1:30 and most preferably between 1:10 and 1:20.

Preferably, the ultrasonic energy output of ultrasonic transducer 10 has a frequency in a range of 50 KHz–1000

KHz, more preferably between 100 KHz-500 KHz and most preferably between 150 KHz-300 KHz.

Preferably, each high amplitude portion 112 is comprised of between 2 and 1000 sequential cycles at an amplitude above the cavitation maintaining threshold 120, more preferably between 25 and 500 sequential cycles at an amplitude above the cavitation maintaining threshold 120 and most preferably between 100 and 300 sequential cycles at an amplitude above the cavitation maintaining threshold 120.

Figure 3A:
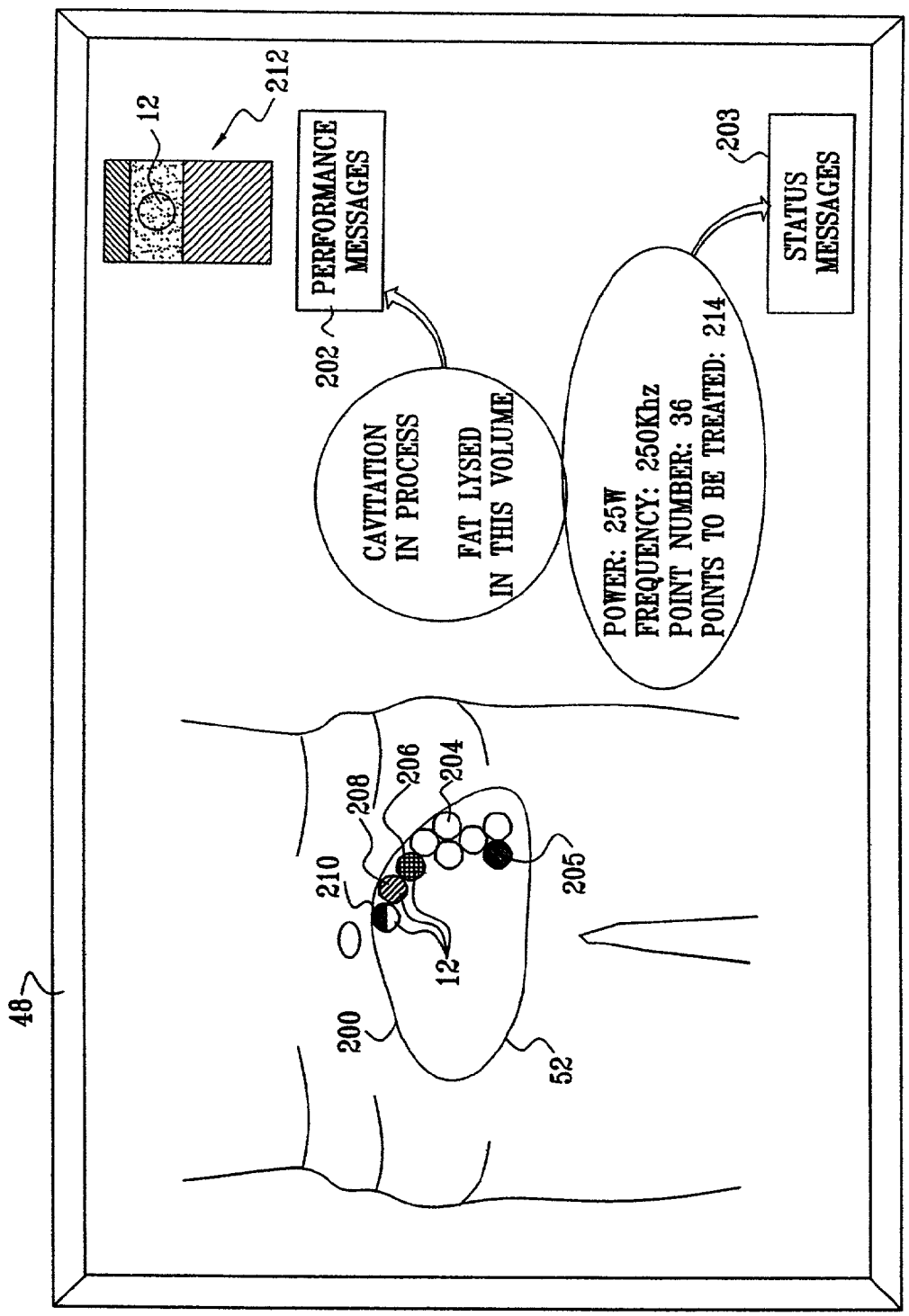
FIGS. 3A and 3B are simplified pictorial illustrations of the appearance of an operator interface display during normal operation and faulty operation respectively.
Figure 3B:
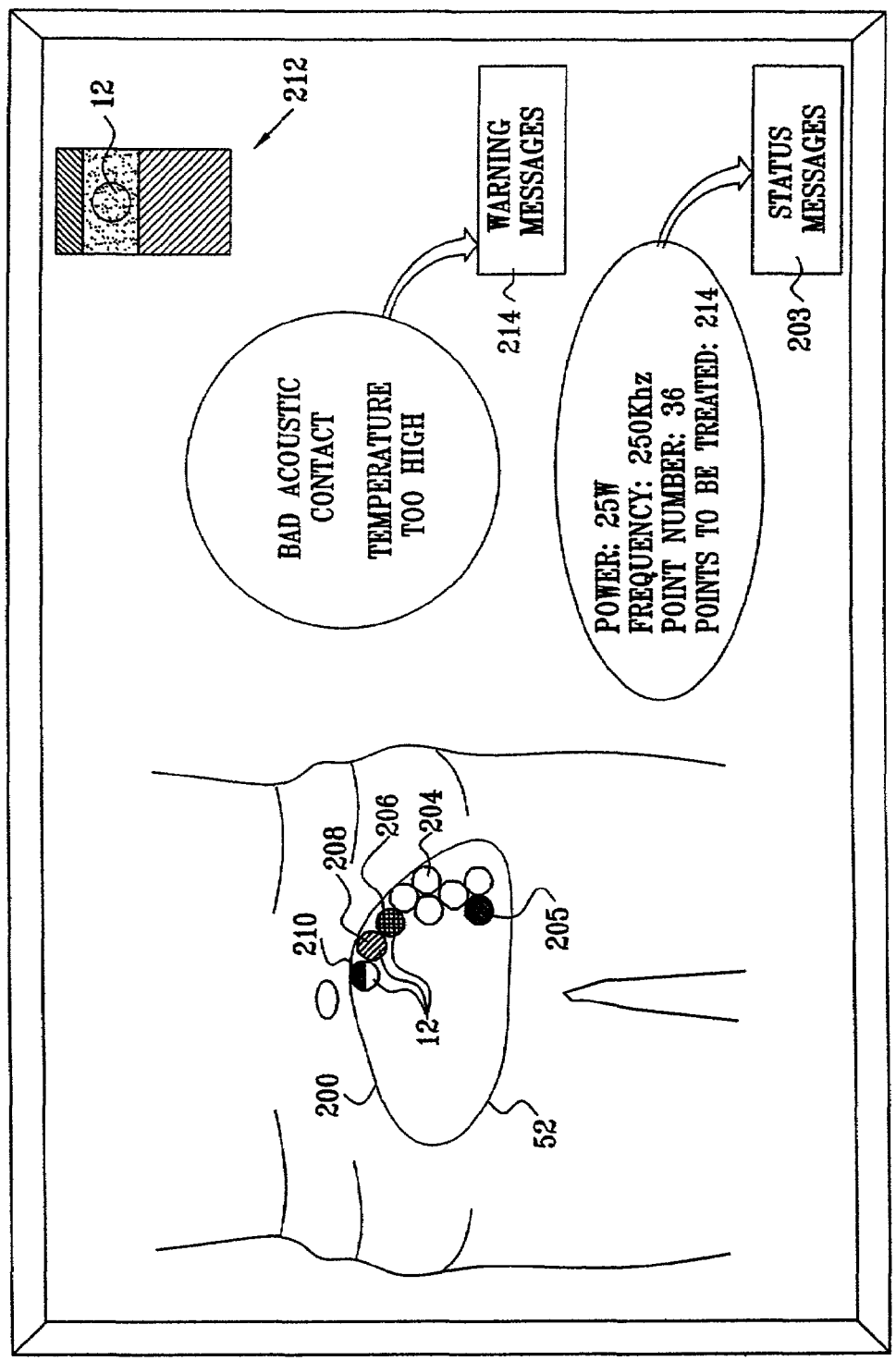

Reference is now made to FIGS. 3A and 3B, which are simplified pictorial illustrations of the appearance of an operator interface display during normal operation and faulty operation respectively. As seen in FIG. 3A, during normal operation, display 48 typically shows a plurality of target volumes 12 (FIG. 1) within a calculated target region 200, typically delimited by outline representation 52 (FIG. 1). Additionally, display 48 preferably provides one or more pre-programmed performance messages 202 and status messages 203.

It is seen the various target volumes 12 are shown with different shading in order to indicate their treatment status. For example, unshaded target volumes, here designated by reference numerals 204 have already experienced lipolysis. A blackened target volume 12, designated by reference numeral 205 is the target volume next in line for lipolysis. A partially shaded target volume 206 typically represents a target volume which has been insufficiently treated to achieve complete lipolysis, typically due to an insufficient treatment duration.

Other types of target volumes, such as those not to be treated due to insufficient presence of adipose tissue therein or for other reasons, may be designated by suitable colors or other designations, and are here indicated by reference numerals 208 and 210.

Typical performance messages 202 may include "CAVITATION IN PROCESS" and "FAT LYSED IN THIS VOLUME". Typical status messages 203 may include an indication of the power level, the operating frequency, the number of target volumes 12 within the calculated target region 200 and the number of target volumes 12 which remain to undergo lipolysis.

Display 48 also preferably includes an graphical cross sectional indication 212 derived from an ultrasonic image preferably provided by imaging ultrasonic transducer sub-assembly 23 (FIG. 1). Indication 212 preferably indicates various tissues in the body in cross section and shows the target volumes 12 in relation thereto. In accordance with a preferred embodiment of the present invention, indication 212 may also provide a visually sensible indication of cavitation within the target volume 12.

Turning to FIG. 3B, it is seen that during abnormal operation, display 48 provides pre-programmed warning messages 214.

Typical warning messages may include "BAD ACOUSTIC CONTACT", "TEMPERATURE TOO HIGH". The "TEMPERATURE TOO HIGH" message typically relates to the skin tissue, although it may alternatively or additionally relate to other tissue inside or outside of the target volume or in transducer 10 (FIG. 1).

Figure 4:
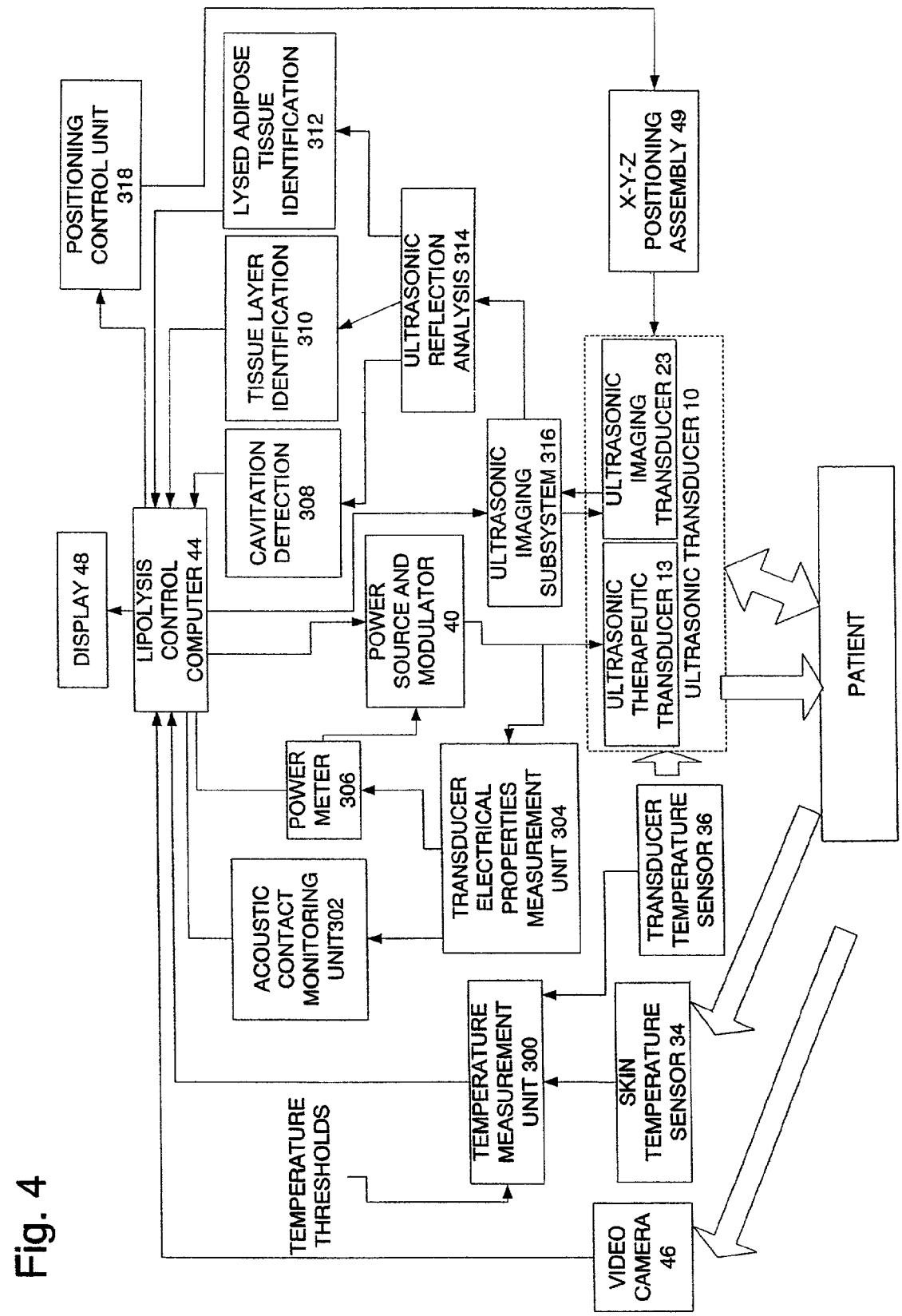
FIG. 4 is a simplified block diagram illustration of an ultrasonic lipolysis system constructed and operative in accordance with a preferred embodiment of the present invention.

Reference is now made to FIG. 4, which illustrates an ultrasonic lipolysis system constructed and operative in accordance with a preferred embodiment of the present invention. As described hereinabove with reference to FIG. 1 and as seen in FIG. 4, the ultrasonic lipolysis system comprises a lipolysis control computer 44 which outputs to a display 48. Lipolysis control computer 44 preferably receives inputs from video camera 46 (FIG. 1) and from a temperature measurement unit 300, which receives temperature threshold settings as well as inputs from skin temperature sensor 34 (FIG. 1) and transducer temperature sensor 36 (FIG. 1). Temperature measurement unit 300 preferably compares the outputs of both sensors 34 and 36 with appropriate threshold settings and provides an indication to lipolysis control computer 44 of exceedance of either threshold.

Lipolysis control computer 44 also preferably receives an input from an acoustic contact monitoring unit 302, which in turn preferably receives an input from a transducer electrical properties measurement unit 304. Transducer electrical properties measurement unit 304 preferably monitors the output of power source and modulator assembly 40 (FIG. 1) to ultrasonic therapeutic transducer 13.

An output of transducer electrical properties measurement unit 304 is preferably also supplied to a power meter 306, which provides an output to the lipolysis control computer 44 and a feedback output to power source and modulator assembly 40.

Lipolysis control computer 44 also preferably receives inputs from cavitation detection functionality 308, tissue layer identification functionality 310 and lysed adipose tissue identification functionality 312, all of which receive inputs from ultrasonic reflection analysis functionality 314. Ultrasonic reflection analysis functionality 314 receives ultrasonic imaging inputs from an ultrasonic imaging sub-system 316, which operates ultrasonic imaging transducer 23 (FIG. 1).

Lipolysis control computer 44 provides outputs to power source and modulator assembly 40, for operating ultrasonic therapeutic transducer 13, and to ultrasonic imaging sub-system 316, for operating ultrasonic imaging transducer 23. A positioning control unit 318 also receives an output from lipolysis control computer 44 for driving X-Y-Z positioning assembly 49 (FIG. 1) in order to correctly position transducer 10, which includes ultrasonic therapeutic transducer 13 and ultrasonic imaging transducer 23.

Figure 5A:
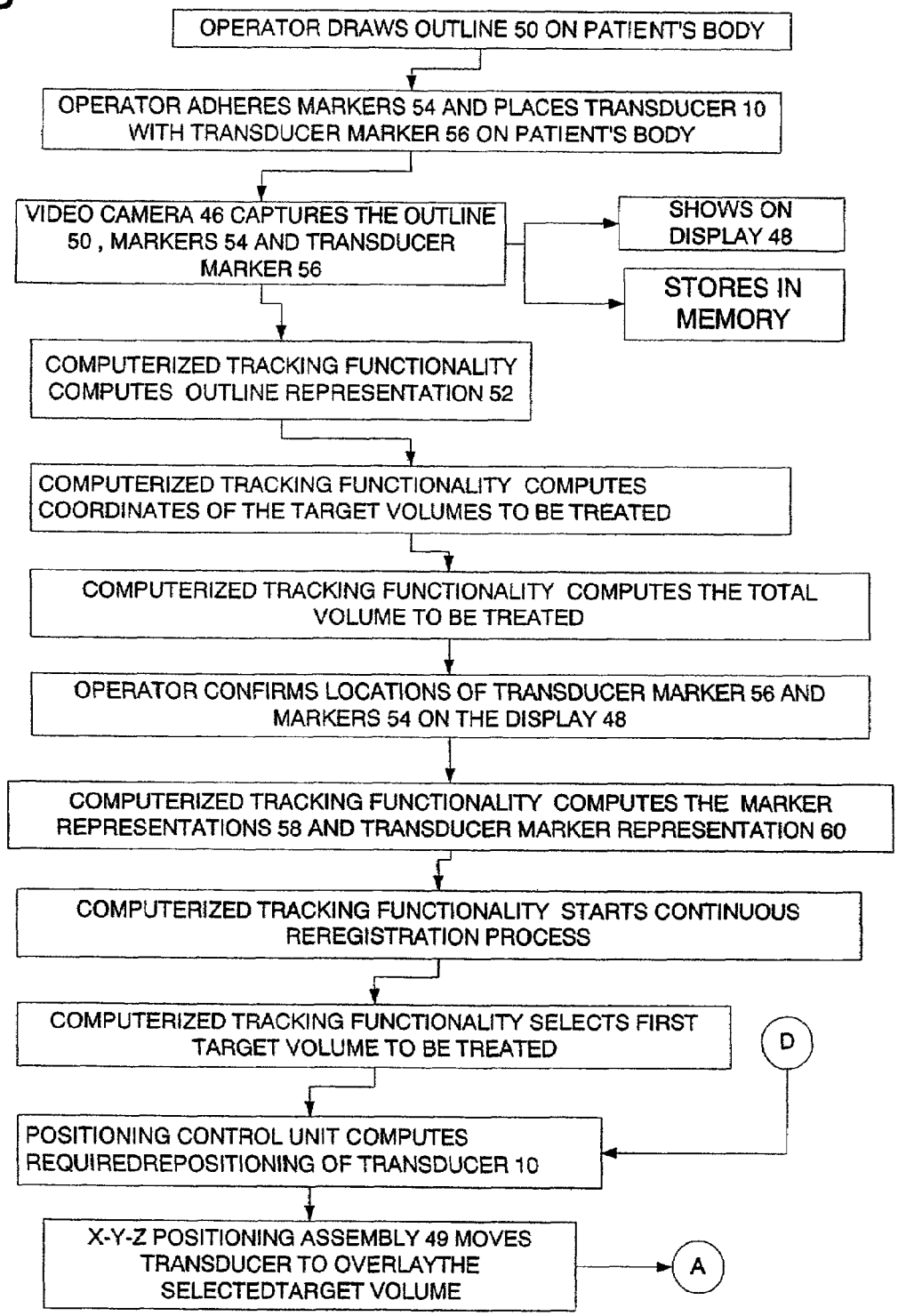
FIGS. 5A, 5B and 5C are together a simplified flowchart illustrating operator steps in carrying out lipolysis in accordance with a preferred embodiment of the present invention.
Figure 5B:
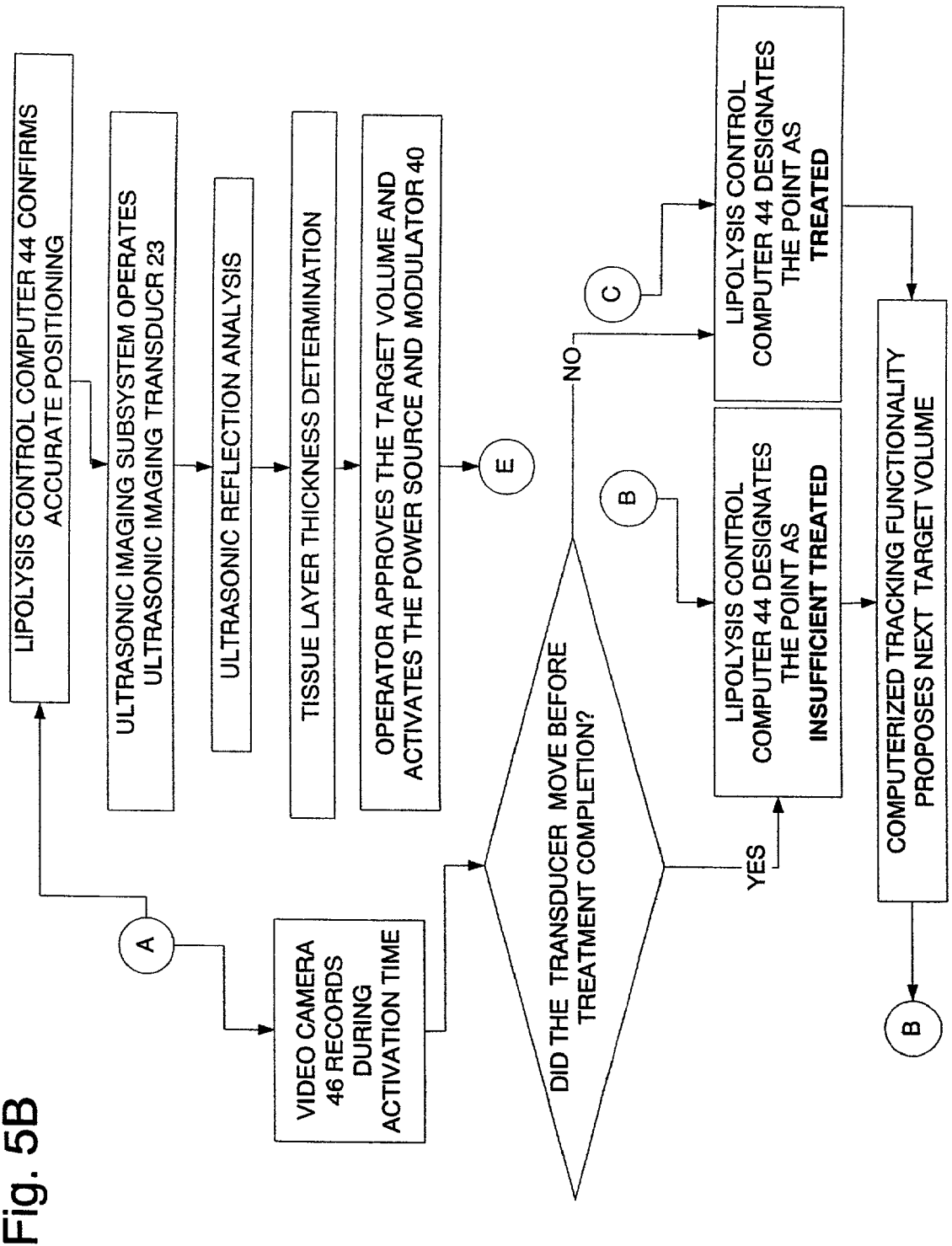
Figure 5C:
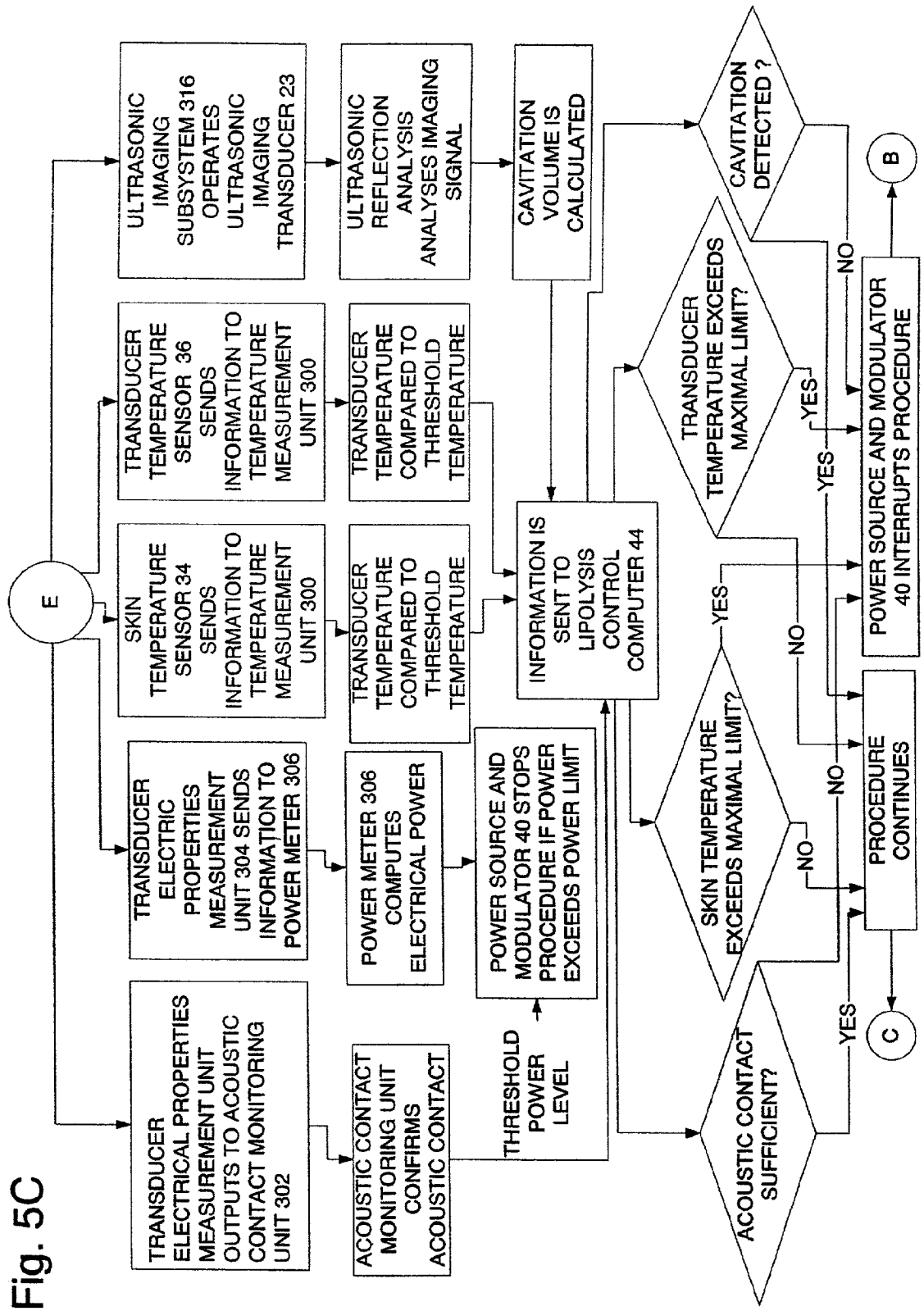

Reference is now made to FIGS. 5A, 5B and 5C, which are together a simplified flowchart illustrating operator steps in carrying out lipolysis in accordance with a preferred embodiment of the present invention. As seen in FIG. 4A, initially an operator preferably draws an outline 50 (FIG. 1) on a patient's body. Preferably, the operator also adheres stereotactic markers 54 (FIG. 1) to the patient's body and places transducer 10, bearing marker 56, at a desired location within outline 50.

Camera 46 (FIG. 1) captures outline 50 and markers 54 and 56. Preferably, outline 50 and markers 54 and 56 are displayed on display 48 in real time. The output of camera 46 is also preferably supplied to a memory associated with lipolysis control computer 44 (FIG. 1).

A computerized tracking functionality preferably embodied in lipolysis control computer 44 preferably employs the output of camera 46 for computing outline representation 52, which may be displayed for the operator on display 48. The computerized tracking functionality also preferably computes coordinates of target volumes for lipolysis treatment, as well as adding up the total volume of tissue sought to undergo lipolysis.

Preferably, the operator confirms the locations of markers 54 and 56 on display 48 and the computerized tracking functionality calculates corresponding marker representations 58 and 60.

In accordance with a preferred embodiment of the present invention the computerized tracking functionality employs markers 54 and marker representations 58 for continuously maintaining registration of outline 50 with respect to outline representation 52, and thus of target volumes 12 with respect to the patient's body, notwithstanding movements of the patients body during treatment, such as due to breathing or any other movements, such as the patient leaving and returning to the treatment location.

The computerized tracking functionality selects an initial target volume to be treated and positioning control unit 318 (FIG. 4), computes the required repositioning of transducer 10. X-Y-Z positioning assembly 49 repositions transducer 10 to overlie the selected target volume.

Referring additionally to FIG. 5B, it is seen that following repositioning of transducer 10, the lipolysis control computer 44 confirms accurate positioning of transducer 10 with respect to the selected target volume. The ultrasonic imaging subsystem 316 (FIG. 4) operates ultrasonic imaging transducer 23, causing it to provide an ultrasonic reflection analysis functionality 314 for analysis.

Based on an output from ultrasonic reflection analysis functionality 314, the thicknesses of the various tissue layers of the patient are determined. Upon receiving an indication of the tissue layer thicknesses, an operator may approve the selected target volume and activates the power source and modulator assembly 40 (FIG. 1).

Turning additionally to FIG. 5C, it is seen that the following functionalities take place:

Transducer electrical properties measurement unit 304 provides an output to acoustic contact monitoring unit 302, which determines whether sufficient acoustic contact with the patient is present, preferably by analyzing the current and voltage at therapeutic transducer 13.

Transducer electrical properties measurement unit 304 provides an output to power meter 306, which computes the average electrical power received by the therapeutic transducer 13. If the average electrical power received by the therapeutic transducer 13 exceeds a predetermined threshold, operation of the power source and modulator assembly 40 may be automatically terminated.

Skin temperature sensor 34 measures the current temperature of the skin at transducer 10 and supplies it to temperature measurement unit 300, which compares the skin temperature to the threshold temperature. Similarly, transducer temperature sensor 36 measures the current temperature at transducer 10 and supplies it to temperature measurement unit 300, which compares the transducer temperature to the threshold temperature. The outputs of temperature measurement unit 300 are supplied to lipolysis control computer 44.

The ultrasonic imaging subsystem 316 operates ultrasonic imaging transducer 23 and receives an imaging output, which is analyzed by ultrasonic reflection analysis functionality 314. The result of this analysis is employed for cavitation detection and a cavitation detection output is supplied to lipolysis control computer 44.

Should any of the following four conditions occur, the power source and modulator assembly 40 automatically terminates operation of therapeutic transducer 13. Should none of the following conditions occur, the automatic operation of power source and modulator assembly 40 continues:
1. Acoustic contact is insufficient.
2. Skin temperature exceeds threshold temperature level.
3. Transducer 13 temperature exceeds threshold temperature level.
4. Cavitation is not detected.

Returning to FIG. 5B, it is noted that during automatic operation of power source and modulator assembly 40, video camera 46 preferably records the target region and notes whether the transducer 10 remained stationary during the entire treatment duration of the selected target volume 12. If so, and if none of the aforesaid four conditions took place, lipolysis control computer 44 confirms that the selected target volume was treated. The computerized tracking functionality of lipolysis control computer 44 then proposes a further target volume 12 to be treated.

If, however, the transducer 10 did not remain stationary for a sufficient duration, the selected target volume is designated by lipolysis control computer 44 as having been insufficiently treated.

It is appreciated that by using multiple transducers multiplicity of target volumes can be treated at various time patterns such as sequential time patterns or partially overlapping time patterns.

It is also appreciated that the multiplicity of target volumes may also overlap in space or partially overlap in space.

The currently available best mode of the computational tracking functionality is set forth in Appendix A, includes the following steps:
1) Provide a PC computer, such as an Intel-based Pentium III 800 MHz computer with Microsoft Windows 2000 operating system, a hard disk with a minimal capacity of 10 GB, 1 available PCI slot and a 17" computer screen.
2) Matrox Orion Frame Grabber Hardware installation/configuration:
   a) Remove/Disable the VGA board present in the PC computer.
   b) Place the Matrox Orion Frame Grabber board available from Matrox (1055 boul. St-Regis, Dorval, Quebec Canada H9P 2T4) into an available PCI slot in the PC computer.
   c) Under Microsoft Windows 2000, on booting the computer, Microsoft Windows' Plug-and-Play system detects a new Multimedia Video Device and requests to assign it a driver. At this point, click Cancel.
   d) Install the JAI CV-S3200 DSP Surveillance Color CCD Camera available from JAI America Inc., 23046 Avenida de la Carlota, Suite 450, Laguna Hills, Calif. 92653 United States and connect to the Matrox Orion Framer Grabber.
   e) Set the computer screen impedance switches, red, green, and blue inputs to 75 ohms.
   f) Set the computer screen synchronization inputs to high impedance and external sync mode.
   g) Connect the computer screen to Matrox Orion's 15-pin female VGA output connector (DB-15).
3) Matrox MIL-Lite software (version 6.1) installation:
   a) Run the Matrox MIL-Lite setup.exe program and follow the default prompts .
   b) Run the Matrix Expansion Pack (version 1.0).
   c) Choose "PAL-YC mode of grabbing" when prompted
   d) Establish the RS-232 serial communication between the PC and the JAI camera by registering and installing the "JAI Camera ActiveX object"
4) Track Software Installation:
   a) Create the following respective directories:
      1) <Track root>—a root directory for Track project
      2) <Track root>\Src—contains source code files
      3) <Track root>\Debug—contains an executable file for Track project
      4) <Track root>\Images—contains BMP files for debugging the interior region detection process.
      5) <Track root>\Log—contains log files and BMP image of the scene
      6) <Track root>\Timing—contains timing data files for debugging b) Copy the file TRACKOBJ.HEX in the \apndx-A folder stored in the appended CD-ROM into a temporary directory.

c) Unhex the computer listing TRACKOBJ.HEX using HEX IT V1.8 or greater by John Augustine, 3129 Earl St., Laureldale, Pa. 19605 creating file TRACKOBJ.ZIP d) Decompress the file TRACKOBJ.ZIP using WINZIP version 6.2 or greater, extracting all files into a temporary directory essentially extracting the following file objects:
1) CAMERADLG.OBJ
2) DISPLAYFUNCS.OBJ
3) IMAGEPROC.OBJ
4) INTERIORREGION.OBJ
5) MARKERS.OBJ
6) NODES.OBJ
7) PARAMETERSDLG.OBJ
8) STDAFX.OBJ
9) TRACK.OBJ
10) TRACK.RES
11) TRACKDLG.OBJ
12) TRANSDUCER.OBJ
13) UTILS.OBJ
14) VIDEOMATROX.OBJ e) Compile the Object code stored in the temporary directory created in step 4*d* using Microsoft Visual C++ compiler version 6.0 The resulting application is created: TRACK.EXE f) To run the Track software, execute the program TRACK.EXE and follow the on-line help to operate the program.

It will be appreciated by persons skilled in the art that the present invention is not limited by what has been particularly shown and described hereinabove. Rather the scope of the present invention includes both combinations and sub-combinations of the various features described hereinabove as well as variations and modifications which would occur to persons skilled in the art upon reading the specification and which are not in the prior art.

The invention claimed is:

1. A method for lysing adipose tissue comprising the steps of:
Directing focused ultrasonic energy at a target volume containing both adipose tissue and non-adipose tissue in a region of the body containing adipose tissue; and
modulating said focused ultrasonic energy so as to selectively lyse at least most of said adipose tissue in said target volume and not lyse non-adipose tissue in said target volume which receives said ultrasonic energy.

2. A method for lysing adipose tissue according to claim 1 and wherein said directing focused ultrasonic energy generally prevents lysis of tissue outside of said target volume.

3. A method for lysing adipose tissue according to claim 1 and also comprising: ultrasonic imaging of said region at least partially concurrently with directing said focused ultrasonic energy at said target volume.

4. A method for lysing adipose tissue according to claim 1 and wherein said directing comprises positioning at least one ultrasonic transducer relative to said body in order to direct said focused ultrasonic energy at said target volume.

5. A method for lysing adipose tissue according to claim 1 and wherein said directing comprises varying the focus of at least one ultrasonic transducer in order to direct said focused ultrasonic energy at said target volume.

6. A method for lysing adipose tissue according to claim 5 and wherein varying the focus changes the volume of said target volume.

7. A method for lysing adipose tissue according to claim 5 and wherein varying the focus changes the distance of said target volume from said at least one ultrasonic transducer.

8. A method for lysing adipose tissue according to claim 3 and wherein said directing comprises positioning at least one ultrasonic transducer relative to said body in order to direct said focused ultrasonic energy at said target volume.

9. A method for lysing adipose tissue according to claim 3 and wherein said directing comprises varying the focus of at least one ultrasonic transducer in order to direct said focused ultrasonic energy at said target volume.

10. A method for lysing adipose tissue according to claim 9 and wherein varying the focus changes the volume of said target volume.

11. A method for lysing adipose tissue according to claim 9 and wherein varying the focus changes the distance of said target volume from said at least one ultrasonic transducer.

12. A method for lysing adipose tissue according to claim 1 and also comprising sensing ultrasonic energy coupling to an external surface of said body adjacent said target volume.

13. A method for lysing adipose tissue according to claim 1 and also comprising sensing of cavitation at said target volume.

14. A method for lysing adipose tissue according to claim 3 and also comprising sensing ultrasonic energy coupling to an external surface of said body adjacent said target volume.

15. A method for lysing adipose tissue according to claim 3 and also comprising sensing of cavitation at said target volume.

16. A method according to claim 1 and wherein said directing takes place from an ultrasonic transducer located outside of the body.

17. A method according to claim 3 and wherein said directing takes place from an ultrasonic transducer located outside of the body.

18. A method according to claim 1 and wherein said ultrasonic energy has a frequency in a range of 50 KHz-1000 KHz.

19. A method according to claim 1 and wherein said ultrasonic energy has a frequency in a range of 100 KHz-500 KHz.

20. A method according to claim 1 and wherein said ultrasonic energy has a frequency in a range of 150 KHz300 KHz.

21. A method according to claim 1 and wherein said modulating provides a duty cycle between 1:2 and 1:250.

22. A method according to claim 1 and wherein said modulating provides a duty cycle between 1:5 and 1:30.

23. A method according to claim 1 and wherein said modulating provides a duty cycle between 1:10 and 1:20.

24. A method according to claim 20 and wherein said modulating provides a duty cycle between 1:10 and 1:20.

25. A method according to claim 1 and wherein said modulating provides between 2 and 1000 sequential cycles at an amplitude above a cavitation threshold.

26. A method according to claim 1 and wherein said modulating provides between 25 and 500 sequential cycles at an amplitude above a cavitation threshold.

27. A method according to claim 1 and wherein said modulating provides between 100 and 300 sequential cycles at an amplitude above a cavitation threshold.

28. A method according to claim 20 and wherein said modulating provides between 100 and 300 sequential cycles at an amplitude above a cavitation threshold.

29. A method according to claim 24 and wherein said modulating provides between 100 and 300 sequential cycles at an amplitude above a cavitation threshold.

30. A method according to claim 1 and wherein said modulating comprises modulating the amplitude of said ultrasonic energy over time.

31. A method according to claim 3 and wherein said ultrasonic energy has a frequency in a range of 50 KHz-1000 KHz.

32. A method according to claim 3 and wherein said ultrasonic energy has a frequency in a range of 100 KHz-500 KHz.

33. A method according to claim 3 and wherein said ultrasonic energy has a frequency in a range of 150 KHz-300 KHz.

34. A method according to claim 3 and wherein said modulating provides a duty cycle between 1:2 and 1:250.

35. A method according to claim 3 and wherein said modulating provides a duty cycle between 1:5 and 1:30.

36. A method according to claim 3 and wherein said modulating provides a duty cycle between 1:10 and 1:20.

37. A method according to claim 33 and wherein said modulating provides a duty cycle between 1:10 and 1:20.

38. A method according to claim 3 and wherein said modulating provides between 2 and 1000 sequential cycles at an amplitude above a cavitation threshold.

39. A method according to claim 3 and wherein said modulating provides between 25 and 500 sequential cycles at an amplitude above a cavitation threshold.

40. A method according to claim 3 and wherein said modulating provides between 100 and 300 sequential cycles at an amplitude above a cavitation threshold.

41. A method according to claim 33 and wherein said modulating provides between 100 and 300 sequential cycles at an amplitude above a cavitation threshold.

42. A method according to claim 37 and wherein said modulating provides between 100 and 300 sequential cycles at an amplitude above a cavitation threshold.

43. A method according to claim 3 and wherein said modulating comprises modulating the amplitude of said ultrasonic energy over time.

44. A method for lysing adipose tissue comprising the steps of:
   directing ultrasonic energy at a multiplicity of target volumes within a region of a body, which target volumes contain adipose tissue and non-adipose tissue, thereby to selectively lyse at least most of said adipose tissue within said target volumes and generally not lyse non-adipose tissue within said target volumes which receives said ultrasonic energy; and
   computerized tracking of said multiplicity of target volumes notwithstanding movement of said body.

45. A method for lysing adipose tissue according to claim 44 and wherein said computerized tracking includes sensing changes in the position of markings on said body and employing sensed changes for tracking the positions of said target volumes in said body.

46. Apparatus for lysing adipose tissue comprising:
   A focused ultrasonic energy director, directing focused ultrasonic energy at a target volume in a region of a body containing adipose and non-adipose tissue; and
   a modulator, cooperating with said energy director to produce a focused ultrasonic energy such that at least most of said adipose tissue within said target volume is lysed and non-adipose tissue within said target volume which receives said ultrasonic energy is not lysed.

47. Apparatus for lysing adipose tissue according to claim 46 and wherein said director generally prevents lysis of tissue outside of said target volume.

48. Apparatus for lysing adipose tissue according to claim 46 and also comprising: an ultrasonic imager providing ultrasonic imaging of said region at least partially concurrently with directing said focused ultrasonic energy at said target volume.

49. Apparatus for lysing adipose tissue according to claim 46 and wherein said director comprises a positioner, positioning at least one ultrasonic transducer relative to said body in order to direct said focused ultrasonic energy at said target volume.

50. Apparatus for lysing adipose tissue according to claim 46 and wherein said director varies the focus of at least one ultrasonic transducer in order to direct said focused ultrasonic energy at said target volume.

51. Apparatus for lysing adipose tissue according to claim 50 and wherein varying the focus changes the volume of said target volume.

52. Apparatus for lysing adipose tissue according to claim 50, and wherein varying the focus changes the distance of said target volume from said at least one ultrasonic transducer.

53. Apparatus for lysing adipose tissue according to claim 48 and wherein said director positions at least one ultrasonic transducer relative to said body in order to direct said focused ultrasonic energy at said target volume.

54. Apparatus for lysing adipose tissue according to claim 48 and wherein said director varies the focus of at least one ultrasonic transducer in order to direct said focused ultrasonic energy at said target volume.

55. Apparatus for lysing adipose tissue according to claim 54 and wherein varying the focus changes the volume of said target volume.

56. Apparatus for lysing adipose tissue according to claim 54 and wherein varying the focus changes the distance of said target volume from said at least one ultrasonic transducer.

57. Apparatus for lysing adipose tissue according to claim 46 and also comprising a sensor, sensing ultrasonic energy coupling to an external surface of said body adjacent said target volume.

58. Apparatus for lysing adipose tissue according to claim 46 and also comprising a sensor, sensing of cavitation at said target volume.

59. Apparatus for lysing adipose tissue according to claim 48 and also comprising a sensor, sensing ultrasonic energy coupling to an external surface of said body adjacent said target volume.

60. Apparatus for lysing adipose tissue according to claim 48 and also comprising a sensor, sensing of cavitation at said target volume.

61. Apparatus according to claim 46 and wherein said director comprises an ultrasonic transducer located outside of the body.

62. Apparatus according to claim 48 and wherein said director comprises an ultrasonic transducer located outside of the body.

63. Apparatus according to claim 46 and wherein said ultrasonic energy has a frequency in a range of 50 KHz-1000 KHz.

64. Apparatus according to claim 46 and wherein said ultrasonic energy has a frequency in a range of 100 KHz-500 KHz.

65. Apparatus according to claim and wherein said ultrasonic energy has a frequency in a range of 150 KHz-300 KHz.

66. Apparatus according to claim 46 and wherein said modulator provides a duty cycle between 1:2 and 1:250.

67. Apparatus according to claim 46 and wherein said modulator provides a duty cycle between 1:5 and 1:30.

68. Apparatus according to claim 46 and wherein said modulator provides a duty cycle between 1:10 and 1:20.

69. Apparatus according to claim 65 and wherein said modulator provides a duty cycle between 1:10 and 1:20.

70. Apparatus according to claim 46 and wherein said modulator provides between 2 and 1000 sequential cycles at an amplitude above a cavitation threshold.

71. Apparatus according to claim 46 and wherein said modulator provides between 25 and 500 sequential cycles at an amplitude above a cavitation threshold.

72. Apparatus according to claim 46 and wherein said modulator provides between 100 and 300 sequential cycles at an amplitude above a cavitation threshold.

73. Apparatus according to claim 65 and wherein said modulator provides between 100 and 300 sequential cycles at an amplitude above a cavitation threshold.

74. Apparatus according to claim 69 and wherein said modulator provides between 100 and 300 sequential cycles at an amplitude above a cavitation threshold.

75. Apparatus according to claim 46 and wherein said modulator modulates the amplitude of said ultrasonic energy over time.

76. Apparatus according to claim 48 and wherein said ultrasonic energy has a frequency in a range of 50 KHz-1000 KHz.

77. Apparatus according to claim 48 and wherein said ultrasonic energy has a frequency in a range of 100 KHz-500 KHz.

78. Apparatus according to claim 48 and wherein said ultrasonic energy has a frequency in a range of 150 KHz-300 KHz.

79. Apparatus according to claim 48 and wherein said modulator provides a duty cycle between 1:2 and 1:250.

80. Apparatus according to claim 48 and wherein said modulator provides a duty cycle between 1:5 and 1:30.

81. Apparatus according to claim 48 and wherein said modulator provides a duty cycle between 1:10 and 1:20.

82. Apparatus according to claim 78 and wherein said modulator provides a duty cycle between 1:10 and 1:20.

83. Apparatus according to claim 48 and wherein said modulator provides between 2 and 1000 sequential cycles at an amplitude above a cavitation threshold.

84. Apparatus according to claim 48 and wherein said modulator provides between 25 and 500 sequential cycles at an amplitude above a cavitation threshold.

85. Apparatus according to claim 48 and wherein said modulator provides between 100 and 300 sequential cycles at an amplitude above a cavitation threshold.

86. Apparatus according to claim 78 and wherein said modulator provides between 100 and 300 sequential cycles at an amplitude above a cavitation threshold.

87. Apparatus according to claim 82 and wherein said modulator provides between 100 and 300 sequential cycles at an amplitude above a cavitation threshold.

88. Apparatus according to claim 48 and wherein said modulator modulates the amplitude of said ultrasonic energy over time.

89. Apparatus for lysing adipose tissue comprising:
A director, directing ultrasonic energy at a miltiplicity of target volumes within a region of a body, which target volumes contain adipose tissue and non-adipose tissue, a modulator,—cooperating with said energy director to produce focused ultrasonic energy—thereby to lyse at least most of said adipose tissue within said target volumes and not lyse non-adipose tissue within said target volumes which receives said ultrasonic energy; and computerized tracking functionality providing computerized tracking of said miltiplicity of target volumes notwithstanding movement of said body.

90. Apparatus for lysing adipose tissue according to claim 89 and wherein said computerized tracking functionality is operative to sense changes in the position of markings on said body and to employ sensed changes for tracking the positions of said target volumes in said body.

* * * * *